(12) United States Patent
Moruzzi et al.

(10) Patent No.: US 6,695,766 B2
(45) Date of Patent: Feb. 24, 2004

(54) MAGNETIC EMBRYO TRANSFER

(75) Inventors: James F. Moruzzi, Olympia, WA (US); Shelton X. Cai, Olympia, WA (US)

(73) Assignee: Olympia Womens Health, Olympia, WA (US)

( * ) Notice: Subject to any disclaimer, the term of this patent is extended or adjusted under 35 U.S.C. 154(b) by 0 days.

(21) Appl. No.: 10/133,220

(22) Filed: Apr. 26, 2002

(65) Prior Publication Data

US 2003/0204128 A1 Oct. 30, 2003

(51) Int. Cl.$^7$ ............................................... A61B 17/43
(52) U.S. Cl. ......................................................... 600/34
(58) Field of Search ........................... 600/34; 604/514, 604/515

(56) References Cited

U.S. PATENT DOCUMENTS

| | | |
|---|---|---|
| 5,084,004 A | 1/1992 | Ranoux |
| 5,360,389 A | 11/1994 | Chenette |
| 5,961,444 A | 10/1999 | Thompson |
| 6,100,249 A | 8/2000 | Macnamee |
| 6,196,965 B1 | 3/2001 | Purdum |
| 6,319,192 B1 | 11/2001 | Engel et al. |

OTHER PUBLICATIONS

Gardner et al., "Culture and transfer of human blastocysts increases implantation rates and reduces the need for multiple embryo transfers," *Fertility and Sterility*, 1998, 69:84–88.
Gardner et al., "A prospective randomized trial of blastocyst culture and transfer in in–vitro fertilization," *Human Reproduction*, 1998, 13(12):3434–3440.
Jones et al., "The program for in vitro fertilization at Norfolk," *Fertility and Sterility*, 1982, 38:14–21.
Steptoe and Edwards, "Birth After the Reimplantation of a Human Embryo," *Lancet*, 1978, 2(8084):366.
Wortham, Jr. et al., "Vital initiation of pregnancy (VIP) using human menopausal gonadotropin and human chorionic gonadotropin ovulation induction: Phase 1—1981," *Fertility and Sterility*, 1983, 39(6):785–792.

*Primary Examiner*—John P. Lacyk
(74) *Attorney, Agent, or Firm*—Fish & Richardson P.C., P.A.

(57) ABSTRACT

The invention provides (1) a method for stabilizing an egg or embryo in the uterus of a female mammal, (2) eggs or embryos having improved stability in the uterus, and (3) a method for preparing these eggs or embryos. The invention involves the use of magnetic particles and a magnetic field.

28 Claims, 2 Drawing Sheets

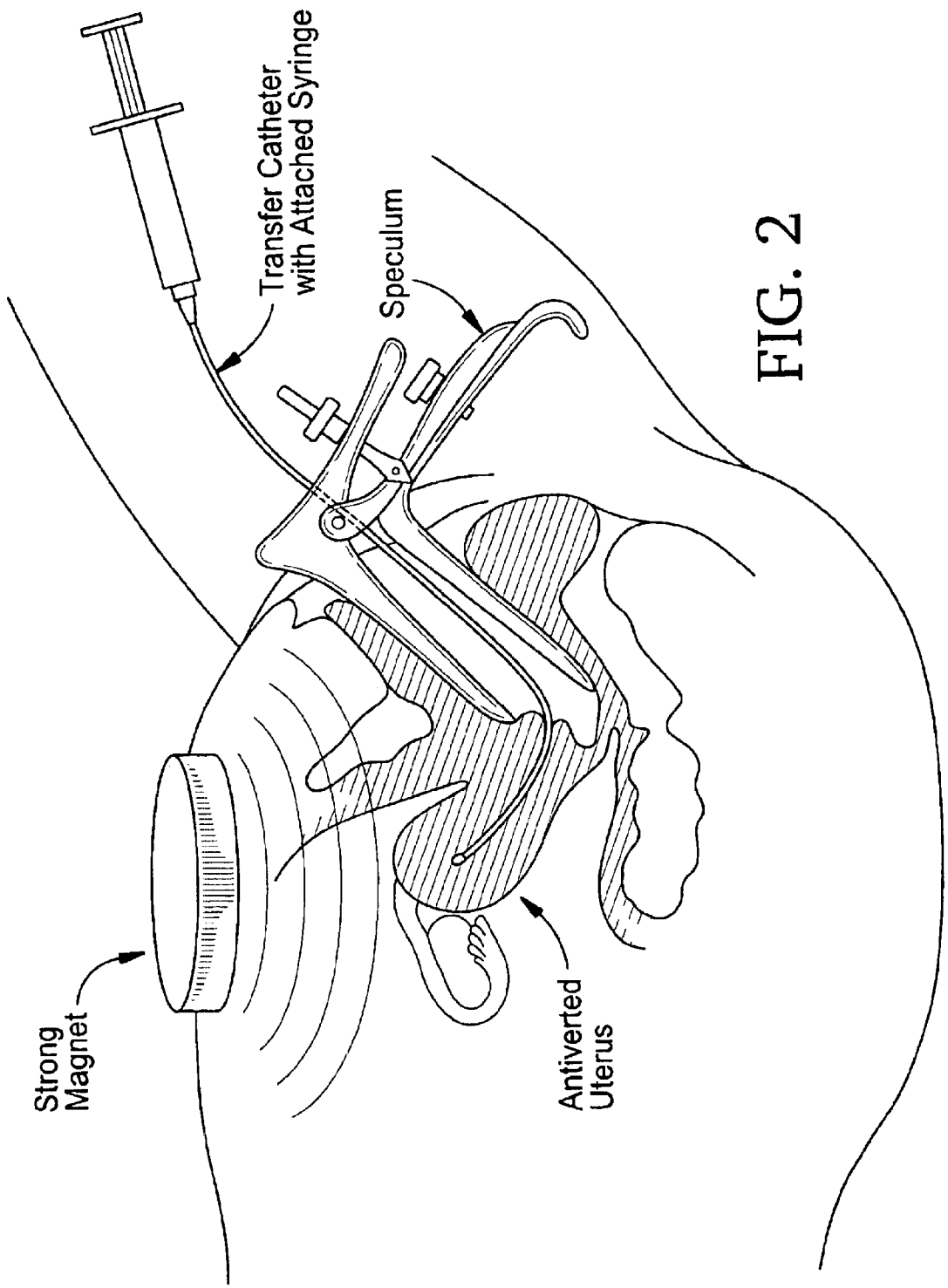

MAGNETIC EMBRYO TRANSFER

BACKGROUND

1. Technical Field

The invention relates to methods and materials involved in aiding implantation of an egg or embryo in the uterus of a female mammal.

2. Background Information

Human in vitro fertilization was initially reported in England around 1978 (see Steptoe & Edwards (1978) Lancet 2:366). Despite its low success rate, in vitro fertilization is generally used as a treatment for infertility as well as for applications involved in selection against genetic diseases. The transfer of more advanced healthy embryos has lead to some improvement in the rate of implantation per embryo (Gardner et al. (1998) Fertility and Sterility 69:84). Improvements in the rate of pregnancy through in vitro fertilization also have been achieved by superovulation and the transfer of multiple embryos (Wortham et al. (1983) Fertility and Sterility 39:785). However, multiple embryo transfers often lead to the generation of multi-fetal pregnancies resulting in obstetrical problems including preterm birth.

SUMMARY

The invention provides materials and methods that can be used to aid implantation of an egg or embryo in the uterus of a female mammal. More particularly, the invention provides improved methods for the transfer of eggs and embryos into the uteri of female mammals, as well as methods for adjusting the positions of eggs and embryos in the uteri. The invention also provides eggs and embryos having improved stability in the uteri of mammals and methods for preparing such eggs and embryos. Methods of the invention involve the use of magnetic particles and a magnetic field.

In some embodiments, the invention provides methods for stabilizing mammalian embryos within the uteri of suitable mammals. These methods involve attaching magnetic particles to mammalian embryos to generate coated embryos, transferring the coated embryos into the uteri of suitable mammals, and then applying magnetic fields to the mammals to stabilize the embryos within the uteri. Embryos can be the embryos of humans. Embryos also can be the embryos of horses, cows, or pigs. Embryos can be embryos at the early or late cleavage stage, at the morula stage, or at the blastocyst stage. One embryo can be transferred at a time, or more than one embryo can be transferred simultaneously.

In some embodiments, embryos can have zonae pellucidae to which magnetic particles can be attached. Magnetic particles can be attached to the zonae pellucidae of embryos by reactions with chemical functional groups or through macromolecules such as avidin molecules, streptavidin molecules, protein A molecules, lectin molecules, and antibodies. The zonae pellucidae can have adherent cells through which magnetic particles are attached. Adherent cells can be spermatozoa or cumulus cells such as coronal cells.

The magnetic particles can be paramagnetic particles. The magnetic field can be generated by a permanent magnet or an electromagnet. Permanent magnets or electromagnets can be external or internal to the mammal. The magnetic field generated by an external magnet can be trans-abdominal, trans-sacral, or trans-lumbar to the mammal. The magnetic field generated by an internal magnet can be trans-rectal, trans-urethral, trans bladder, or intra-abdominal to the mammal. The magnetic field can be applied during, after, or during and after transfer of the embryo.

The invention also provides methods for adjusting the locations of coated embryos within the uteri of mammals. These methods involve applying magnetic fields to mammals containing coated embryos. The magnetic fields have sufficient strengths to affect the locations of the coated embryos. The location of an embryo can be adjusted so that the embryo is in proximity of the endometrium or/and at the uterine fundus of a mammal.

In other embodiments, the invention provides methods for preparing embryos having improved stability in the uteri of mammals. These methods involve contacting embryos with magnetic particles capable of attaching to the embryos. The invention also provides for mammalian embryos coated with magnetic particles. Mammalian embryos can be human embryos. Magnetic particles can be paramagnetic particles.

In yet other embodiments, the invention provides methods for stabilizing mammalian eggs within the uteri of suitable mammals. These methods involve attaching magnetic particles to the external zonae pellucidae of the eggs to generate coated eggs, transferring the coated eggs into the uteri, and applying magnetic fields to the mammals to stabilize the eggs within the uteri. In some of these embodiments, eggs can be unfertilized eggs. Eggs can be human eggs. Eggs can be from a horse, a cow, or a pig. One egg can be transferred at a time, or more than one egg can be transferred simultaneously.

Magnetic particles can be attached to the zonae pellucidae of eggs by reactions with chemical functional groups or through macromolecules such as avidin molecules, streptavidin molecules, protein A molecules, lectin molecules, and antibodies. The zonae pellucidae can have adherent cells through which magnetic particles can be attached. Adherent cells can be spermatozoa or cumulus cells such as coronal cells.

The magnetic particles can be paramagnetic particles, and the magnetic field can be generated by a permanent magnet or an electromagnet. Permanent magnets or electromagnets can be external or internal to the mammal. The magnetic field generated by an external magnet can be trans-abdominal, trans-sacral, or trans-lumbar to the mammal. The magnetic field generated by an internal magnet can be trans-rectal, trans-urethral, trans bladder, or intra-abdominal to the mammal. The magnetic field can be applied during, after, or during and after transfer of the egg.

The invention also provides methods for adjusting the locations of coated eggs within the uteri of mammals. These methods involve applying magnetic fields to mammals containing coated eggs. Magnetic fields have sufficient strengths to affect the locations of the coated eggs. The location of an egg can be adjusted so that the egg is in proximity of the endometrium or/and at the uterine fundus of a mammal.

In other embodiments, the invention provides methods for preparing eggs having improved stability in the uteri of mammals. These methods involve contacting eggs with magnetic particles capable of attaching to these eggs. The invention also provides for mammalian eggs coated with magnetic particles. Mammalian eggs can be human eggs. Magnetic particles can be paramagnetic particles.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is an illustration of a transvaginal embryo transfer into an anteverted uterus using a magnetic field.

DETAILED DESCRIPTION

Figure 1:
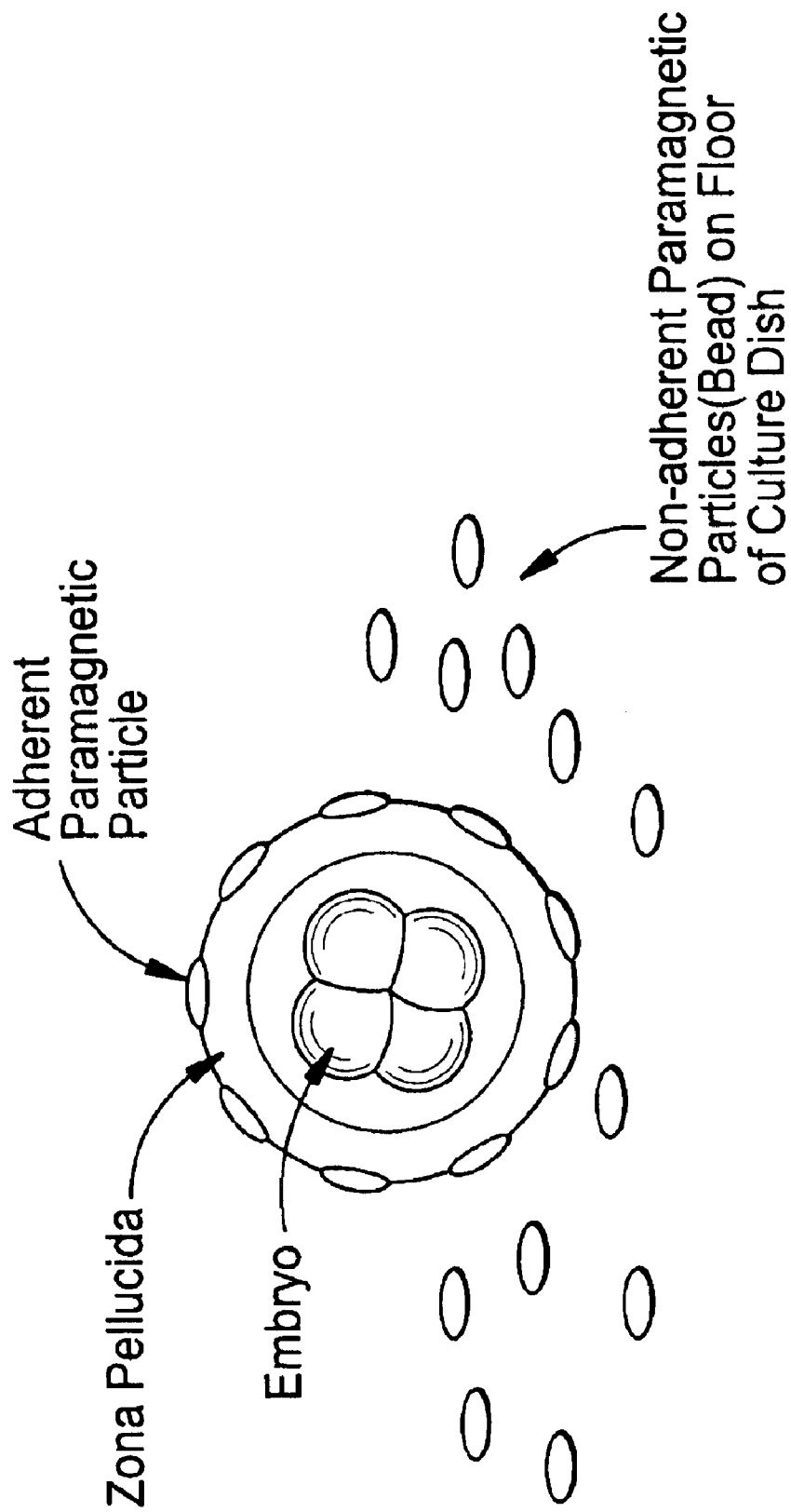
FIG. 1 is a pictorial representation of an embryo being coated with magnetic particles.

The invention provides materials and methods that can be used to aid implantation of an egg or embryo in the uterus of a female mammal. More particularly, the invention provides improved methods for the transfer of eggs and embryos into the uteri of female mammals, as well as methods for adjusting the positions of eggs and embryos in the uteri. The invention also provides eggs and embryos having improved stability in the uteri of mammals and methods for preparing such eggs and embryos. Methods of the invention involve the use of magnetic particles and a magnetic field.

Magnetic Particles and Magnetic Fields

Magnetic particles can be used in the laboratory as solid carriers. Magnetic particles can be either ferromagnetic or paramagnetic, with ferromagnetic particles being relatively more strongly attracted to magnets than paramagnetic particles. Although useful magnetic particles can be made of any magnetic material, typically, particles have cores of iron or iron dioxide with porous or non-porous outer surfaces. Outer surfaces can be, without limitation, silane, glass, or various polymers. One example of a useful surface is borosilicate glass.

The outer surfaces of magnetic particles usually have reactive groups through which magnetic particles can become attached to target substances. Surface reactive groups can be chemical functional groups or macromolecules. Examples of chemical functional groups include —COOH, —NH$_2$, —OH, and —SiOH. Chemical functional groups typically require an activation step prior to reacting with their substrates on target substances. —COOH functional groups, for example, can be activated by reactions with carbodiimide prior to use. Examples of macromolecules that can function as surface reactive groups include avidin or streptavidin, protein A, lectin, and an antibody. A macromolecular reactive group can bind to a general class of molecules or to a particular selected molecule. A reactive group that can bind to a general class of molecules can be, for example, a protein A molecule that binds to the Fc region of an IgG antibody. A reactive group that can bind to a selected molecule can be, for example, a monoclonal antibody specific for a selected antigen. A selected antigen can be a cell surface molecule that is specific to a particular cell type. Without limitation, surface reactive groups useful for performing the methods of the invention can be surface reactive groups that would mediate attachment of magnetic particles to (1) eggs or embryos of interest, and/or (2) the endometrial surface of the uterus of a mammal of interest. Therefore, surface reactive groups include antibodies specific to (1) the zona pellucida of a human egg, (2) cells adherent to the zona pellucida, or (3) the endometrial surface of the uterus of a human patient.

Magnetic particles that have surface reactive groups can be obtained commercially. Magnetic particles that do not have surface reactive groups can be coated with selected surface reactive groups such as monoclonal antibodies using standard methodologies.

Magnetic particles of various sizes can be used to perform the methods of the invention. For example, magnetic particles can have diameters of 0.1, 0.2, 0.4, 0.8, 1.6, 3, 6, 12, 25, 50, 100, 200 or greater than 200 microns. Particularly useful magnetic particles have diameters between about 0.2 to about 200 microns, for example from between about 3 to about 100 microns.

Magnetic particles with surface reactive groups can be used for a number of separation and/or purification applications such as cell separation, nucleic acid isolation, polypeptide purification, immunoassays, solid-phase cDNA library construction or sequencing, and hybridization procedures. Typically, magnetic particles with surface reactive groups are incubated with the target substance to allow for attachment of the magnetic particles to the target substance. The magnetic particle/target substance can be isolated and/or further manipulated using a magnetic field generated by a magnet. The magnet can be selected based on the strength of the magnetic field that it generates. A magnet can be selected for optimal effectiveness in a particular application.

Magnets useful for performing methods of the invention can be permanent magnets or electrical magnets. One example of magnet useful for performing the methods of the invention is the NeoRec-32H magnet (3" diameter, 1" thick; TDK, Inc.).

Eggs and Embryos

Eggs or embryos of the invention can be, without limitation, the eggs or embryos of a mammal such as (1) a human or other primate, (2) a dolphin or other marine mammal, (3) a cow or other farm animal, or (4) a mouse, rat or other rodent.

As used herein, the term "egg" refers to an unfertilized egg as well as a fertilized egg. An unfertilized egg can be isolated from a mammal using known methodologies, e.g., standard methods of follicular aspiration. An unfertilized egg can be fertilized using conventional means. In some embodiments of the invention, an unfertilized egg can be fertilized in vitro by addition of spermatozoa to a culture dish containing the unfertilized egg. In these embodiments, fertilization can be assessed by standard methodologies, for example, by determining the presence of two pronuclei using phase contrast microscopy. In other embodiments of the invention, an unfertilized egg and a sample of spennatozoa can be combined in a procedure used to transfer the unfertilized egg and spermatozoa into the uterus of a mammal. For example, the unfertilized egg can be combined with a sample of spermatozoa in a delivery vehicle such as a catheter for transfer into the uterus. In these embodiments, the unfertilized egg can be fertilized during or subsequent to the transfer step. In some of these embodiments, fertilization can take place in the uterus. In yet other embodiments, the unfertilized egg can be transferred into the uterus of a suitable mammal, and then become fertilized during or after the mammal engages in sexual intercourse.

As used herein, the term "embryo" refers to a multicellular organism, i.e., an organism having two or more cells, at any stage of embryogenesis. Embryos of the invention can include those that initially develop outside a maternal body during the embryo's early stages of development. An embryo of the invention can be an embryo at early or late cleavage, a morula or a blastocyst.

The egg or embryo can be within, or hatched from, its zona pellucida. If present, the zona pellucida can have adhered to it other cell types, herein referred to as adherent cells, to which magnetic particles can attach. The term "adherent cell" refers to any cell type that may be found attached to the zona pellucida of an egg or embryo, for example cumulus cells such as coronal cells. The term "adherent cell," in reference to an egg, also can include a spermatozoon. Alternatively, the zona pellucida can be free of adherent cells.

Suitability of the egg or embryo for successful development in the uterus can be assessed in various ways. For example, the embryo can be examined to determine if timely and even cleavages have taken place. Metabolic activity of the embryo such as the consumption of particular substrates or production of particular metabolites also can be used to determine the suitability of the embryo for successful development in the uterus. In addition, techniques such as blastomere biopsy that provide information related to the genetic status of an egg or embryo can be used to determine whether the egg or embryo is suitable for use in the methods of the invention.

Preparation of Eggs or Embryos for Transfer Into the Uterus of a Mammal

Eggs or embryos can be maintained in a suitable medium and under conditions that have been optimized for a particular species or a particular stage of development. Human embryos, for example, can be cultured in human tubal fluid (HTF) medium containing a suitable amount of human fetal cord serum, e.g. 15%, at 37° C. under 5% $CO_2$. Human embryos in the first 48 hours of development can be cultured in an HTF-based medium such as G1 medium.

An egg or embryo can be prepared for transfer into the uterus of a suitable mammal by coating the egg or embryo with one or more magnetic particles. As used herein, "coating an egg with one or more magnetic particles" refers to attaching one or more magnetic particles having surface reactive groups to a fertilized or unfertilized egg having substrates that can react with the surface reactive groups on the magnetic particles. Similarly, and as used herein, "coating an embryo with one or more magnetic particles" refers to attaching one or more magnetic particles having surface reactive groups to an embryo that has substrates that can react with the surface reactive groups on the magnetic particles. A suitable mammal refers to a mammal from which the egg, or the egg that gave rise to the embryo, is isolated. Alternatively, a suitable mammal can be a mammal of the same species as the mammal from which the egg, or the egg that gave rise to the embryo, is isolated.

An egg or embryo can be coated with one or more magnetic particles by combining the egg, or embryo, and the magnetic particles in an appropriate vessel such as a sterile culture dish such that the egg, or embryo, and the magnetic particles come in contact with, and become attached to, each other. For example, an egg or embryo can be rolled over or mixed with magnetic particles placed in a culture dish.

Magnetic particles can be attached to the egg or embryo indirectly, ie., by attaching to residual adherent cells on the egg or embryo. Alternatively, adherent cells on the egg or embryo can be removed prior to combining the egg or embryo with magnetic particles so that when combined, the magnetic particles attaches directly to the zona pellucida of the egg or embryo. Enzymes such as hyaluronidase, and mechanical methods, such as tight pipetting, can be used to remove adherent cells on an egg or embryo prior to coating of the egg or embryo with magnetic particles.

The medium in which an egg, or embryo, and magnetic particles are combined can be modified to enhance the attachment between the egg, or embryo, and the magnetic particles. For example, a component in the medium such as a buffer, a salt, or a particular polypeptide that may interfere with attachment can be minimized or substituted with a component that enhances, or does not interfere with, attachment. In addition, any feature of a medium that may affect attachment, e.g. the pH, can be adjusted to enhance attachment. Alternatively, a medium that does not have components that would interfere with attachment can be selected.

Delivery of Coated Eggs or Embryos into the Uterus and Stabilization of Eggs or Embryos Within the Uterus An egg or embryo can be transferred to the uterus of a suitable mammal using any delivery vehicle, for example a hollow catheter. Additional examples of delivery vehicles are described in U.S. Pat. Nos. 5,961,444 and 6,196,965. A magnetic field can be used during and/or after transfer of the egg or embryo into the uterine space. The magnetic field can be generated using a magnet that is located externally with respect to the mammal or internally, i.e., within the mammal. An externally located magnet can be above and in contact with, or not in contact with, the surface of the skin. An externally located magnet also can be, without limitation, trans-sacral, trans-abdominal, or trans-lumbar. An internally located magnet is applied from inside the body of the mammal and can be, without limitation, trans-rectal, trans-urethral, trans-bladder, or intra-abdominal. The magnetic field generated from an externally or internally located magnet can be adjusted for an anteverted, a retroverted, or a mid-position uterus. The magnetic field can be applied briefly or for a sustained period. The magnetic field can be applied, for example, until the embryo hatches from the zona pellucida.

Once a coated egg or embryo is transferred into the uterus of a mammal, the magnetic particles coating the egg or embryo and a magnetic field can aid in stabilizing the egg or embryo. A magnetic particle-coated egg or embryo is said to be "stabilized in the uterus" when it is more likely than a non-coated egg or embryo to remain, or implant, in the uterus.

Without being bound by a particular mechanism, magnetic particles and a magnetic field can aid in stabilizing an egg or embryo in the following ways. The magnetic particles coating the egg or embryo confer upon the egg or embryo a greater effective mass, and the resulting physical inertia of the coated egg or embryo aids in retaining the coated egg or embryo in the uterus. In addition, magnetic particles coating the egg or embryo render the egg or embryo responsive to a magnet such that a magnetic field generated using the magnet can be used to prevent the egg or embryo from following the delivery vehicle as the delivery vehicle is removed from the uterus during the transfer procedure. The magnetic field generated using a magnet also can be used to adjust the position of the magnetic particle-coated egg or embryo within the uterus in order to improve the probability of implantation. For example, a magnetic field can be used to position the egg or embryo in close proximity to the endometrium. Furthermore, surface reactive groups on magnetic particles such as chemical functional groups or macromolecular reactive groups can aid in attaching the egg or embryo to the uterine wall.

The invention will be further described in the following examples, which do not limit the scope of the invention described in the claims.

EXAMPLES

Example 1

Effect of Paramagnetic Microparticles on Mammalian Embryos

The effect of paramagnetic microparticles on mammalian embryos was evaluated using mouse embryos. Carboxylated paramagnetic microparticles (12 micron; Polyscience Inc; Catalog number 19233) were applied to the zona pellucida of previously frozen and thawed 2-cell mouse embryos as described below for human embryos. The paramagnetic microparticle-coated mouse embryos developed normally in culture, and hatched from their zona pellucida at the blastocyst stage.

Example 2

Preparation of Patient for Follicle Isolation and Subsequent Embryo Transfer Patients were women who were 35 years old or less, and who were ovulatory with or without clomiphene treatment. Patients had anteverted uteruses and were lacking hydrosalpinx.

The uterus of each patient was sounded with a sterile plastic rod to determine the depth and direction of the uterine fundus from the external cervical os. Follicular growth was monitored with serial transvaginal ultrasound exams. A baseline ultrasound, typically, was performed on cycle day 1 through cycle day 5 of an ovulatory cycle. Cycle day 1 was the first day of menstruation. Daily ultrasound exams were started on cycle day 10 or 11.

When a follicle was 14 mm in diameter on average, daily serum levels of estradiol (E2) and luteinizing hormone (LH) were determined. Follicular aspiration was not performed if a premature LH surge was detected. A follicle was considered to be mature when it was 16 mm or greater, and the serum estradiol level was equal to or greater than 200 pg/mL. If no LH surge occurred and a matured follicle was detected, 10,000 units of human chorionic gonadotropin (HCG) were given intramuscularly, typically, at 10 PM of the same day. In addition, the patient was placed on an indocin treatment regimen consisting of 50 mg of indocin taken by mouth and with food, three times daily. Indocin treatment was stopped before egg retrieval. At 34 hours after the HCG injection, transvaginal follicular aspiration was performed according to the procedure described below. After follicle aspiration, the patient was subjected to a regimen of estradiol treatment that included 2 mg of estradiol tablets taken orally three times daily.

Example 3

Transvaginal Follicular Aspiration

For transvaginal follicular aspiration, the vagina was cleansed with a penicillin and streptomycin containing saline solution. Transvaginal puncture of the mature follicle was performed under direct ultrasound visualization with a disposable double lumen Embryon needle (Sage BioPharmna, Inc.) using an ATL Ultramark IV Plus ultrasound machine. The vaginal probe for ultrasound was covered with a sterile sheath and equipped with a sterile needle guide. The follicle was flushed twice with human tubal fluid (HTF, Irvine Scientific) previously equilibrated to 37° C. in 5% $CO_2$. The egg in its cumulus complex was identified under a dissecting microscope (Wild, Inc.) in a sterile laminar flow hood (Baker, Inc.) The egg was then placed in 1 cc HTF medium with 15% human fetal cord serum in a polystyrene center-well organ culture dish (Falcon 35-3037 and the dish was incubated at 37° C. in 5%, $CO_2$ (Forma Scientific Incubator Model 3195). Activated charcoal filters (CODA, IVF online.com, LLC) were used to ensure purity of the $CO_2$ supply and the air inside the incubator. If an egg was successfully obtained by follicular aspiration, the patient was placed on an estradiol treatment regimen consisting of 2 mg of estradiol taken orally three times daily.

Example 4

In Vitro Fertilization

For in vitro fertilization, seven to eight hours after isolation of the egg, approximately 100,000 motile spermatozoa were added to the culture dish containing the egg. To check for fertilization, the egg was examined for the presence of two pronuclei 18 hours after addition of spermatozoa. The fertilized egg was then cultured in G1.2 medium (Vitrolife Inc.). If unfertilized, a second fertilization attempt was performed. If cleavage of the embryo did not take place at 50 hours after insemination, the embryo was not transferred to a patient.

Example 5

Attachment of Magnetic Particles to an Endometrial Biopsy and to the Zona Pellucida of a Human Embryo Carboxylated microparticles were observed to adhere tightly to the epithelial surface of a human endometrial biopsy when combined in a culture dish. In addition, a preliminary experiment showed that a magnetic force of 500 Gauss (Bm) generated using the NeoRec-32H magnet (3" diameter, 1" thick; TDK, Inc.) did not dislodge paramagnetic particles from the zona pellucida of a human embryo.

Example 6

Preparation of Paramagnetic Microparticle-coated Embryos

Carboxylated paramagnetic microparticles, (12 micron; Polysciences, Inc, Catalog number 19233), were activated according to the manufacture's instructions with some modifications. Briefly, a suspension of carboxylated microparticles was washed in carbonate buffer and then phosphate buffer, reacted with carbodiimide, and the excess carbodiimide was removed by washing with borate buffer as described by the manufacturer's instruction. One droplet of the resulting carboxylated paramagnetic microparticle/borate slurry was added to 3 mL of HTF medium (37° C. in 5% $CO_2$) in a 3.5 cm diameter polystyrene petri dish (Falcon 1008) using a Pasteur pipette. The paramagnetic microparticles were allowed to settle to the bottom of the dish and were concentrated at the center of the dish by swirling the entire dish.

The embryo was prepared by manually removing extraneous coronal cells from the zona pellucida by dissection using two 29-gauge hypodermic needles. The prepared embryo with a minimum of medium was transferred to the dish containing the paramagnetic microparticles using a sterile glass pipette. The embryo was placed onto the activated paramagnetic microparticles and then a dissecting needle was used to roll the embryo over the particles for 30 seconds. The paramagnetic microparticle coated embryo was transferred into G1.2 medium (Vitrolife, Inc.) using a sterile glass pipette and incubated at 37° C. under 5% $CO_2$. The embryo was then inspected for black adherent particles using a dissecting microscope (Wild, Inc.). The embryo was tested for responsiveness to a magnet held outside the culture dish.

Example 7

Transfer of Paramagnetic Microparticle-coated Embryo into a Human Patient

In preparation for embryo transfer, the patient was placed in lithotomy position and a sterile plastic speculum was inserted into the vagina. A preliminary trans-abdominal ultrasound was performed to locate the uterine fundus. The distance between the skin and the fundal endometrium was measured. Prior to the embryo transfer, the cervix of the patient was cleansed using a large cotton swab moistened in penicillin and streptomycin-containing saline.

For embryo transfer, a Wallace transfer catheter (Cooper Surgical, Inc.) was used. The Wallace transfer catheter, with the inner catheter projected 0.5 cm beyond the outer catheter, was shaped to a mild curvature. This resulting transfer catheter was inserted through the cervix such that the end of the outer catheter was placed just within the internal cervical os. Ease of entry for the internal catheter was then tested. Suprapubic pressure over the uterine fundus was sometimes used to facilitate entry of the internal catheter.

The internal catheter was then removed, rinsed in HTF medium, and then loaded with the paramagnetic microparticle coated-embryo in a volume of 30–40 $\mu L$. The internal catheter was then inserted into the uterus through the external Wallace catheter to approximately 1.0 cm from the fundus.

To aid in transfer, the NeoRec-32H magnet was used. The magnet was effective for a distance of 50 to 65 mm. The effective magnetic force was between 125 and 200 Gauss (Bm).

After positioning the tip of the transfer cathether containing the coated embryo 1 cm from the uterine fundus, the magnet was brought from the area of the patient's chest to a location suprapubically above the uterine fundus. The embryo was ejected into the uterus using the syringe attached to the inner Wallace catheter. The inner and outer catheters were held in place for one minute before they were removed. The magnet was kept in place. After the embryologist had inspected the transfer catheter and confirmed that the embryo was discharged successfully, the vaginal speculum was removed. The patient was turned prone with the magnet in place, and then the magnet was removed from its suprapubic location by sweeping cephalad. The patient remained in a recumbent position for two hours, altering between prone or lateral recumbent every half hour.

The patient was instructed to maintain bed rest the day of, and the day following, embryo transfer with the exception of rising to go to the bathroom. The patient also was instructed to refrain from engaging in sexual relations. The night after embryo transfer, progesterone treatment began. The patient was administered a progesterone suppository, 100 mg intravaginally, each night before sleep. Intramuscular progesterone injections (25 mg) were given daily starting at seven days after egg retrieval. A pregnancy test was performed 13 days after egg retrieval. If the pregnancy test was negative, estradiol treatment, initiated after follicular aspiration (see Example 2) and progesterone treatments were stopped. If the pregnancy test was positive, estradiol and progesterone treatments continued every third day. In addition, 2500 units of HCG were admininisted by intramuscular injection every third day.

Embryonic heartbeat at seven weeks of gestation indicated a clinical pregnancy.

Of twelve paramagnetic microparticle-assisted transfers, six clinical pregnancies were obtained. In contrast, the prior art method of embryo transfer using healthy embryos yielded a pregnancy rate of 15% in similar patients. A twin pregnancy was obtained when multiple previously frozen embryos coated with paramagnetic microparticles were transferred. An additional pregnancy has been obtained when a single embryo coated with paramagnetic microparticles was transfer into a woman older than 35 years.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for stabilizing a mammalian embryo within the uterus of a suitable mammal comprising:
   (a) attaching magnetic particles to said embryo to generate a coated embryo;
   (b) transferring said coated embryo into said uterus; and
   (c) applying a magnetic field to said mammal to stabilize said embryo within said uterus.

2. The method of claim 1, wherein said mammal is a human.

3. The method of claim 1, wherein said embryo comprises a zona pellucida.

4. The method of claim 3, wherein said attaching comprises attaching said magnetic particles to said zona pellucida of said embryo.

5. The method of claim 4, wherein said attaching comprises attaching said magnetic particles to said zona pellucida of said embryo by reaction with chemical functional groups.

6. The method of claim 4, wherein said attaching comprises attaching said magnetic particles to said zona pellucida of said embryo by macromolecules selected from the group consisting of avidin molecules, streptavidin molecules, protein A molecules, lectin molecules, and antibodies.

7. The method of claim 3, wherein said zona pellucida further comprises adherent cells.

8. The method of claim 7, wherein said attaching comprises attaching said magnetic particles to said adherent cells.

9. The method of claim 7, wherein said adherent cells are cumulus cells.

10. The method of claim 9, wherein said cumulus cells are coronal cells.

11. The method of claim 7, wherein said adherent cells are spermatozoa.

12. The method of claim 1, wherein said transferring comprises transferring multiple embryos simultaneously.

13. The method of claim 1, wherein said embryo is selected from the group consisting of an embryo at early cleavage stage, an embryo at late cleavage stage, a morula, and a blastocyst.

14. The method of claim 1, wherein said magnetic particles are paramagnetic particles.

15. The method of claim 1, wherein said magnetic field originates from a permanent magnet or an electromagnet.

16. The method of claim 15, wherein said permanent magnet or said electromagnet is external to said mammal.

17. The method of claim 16, wherein said permanent magnet or said electromagnet generates a magnetic field that is trans-abdominal, trans-sacral, or trans-lumbar to said mammal.

18. The method of claim 17, wherein said permanent magnet or said electromagnet is internal to said mammal.

19. The method of claim 18, wherein said permanent magnet or said electromagnet generates a magnetic field that is trans-rectal, trans-urethral, trans bladder, or intra-abdominal to said mammal.

20. The method of claim 1, wherein said applying comprises applying said magnetic field during said transfer of said embryo.

21. The method of claim 1, wherein said applying comprises applying said magnetic field after said transfer of said embryo.

22. The method of claim 1, wherein said applying comprises applying said magnetic field during and after said transfer of said embryo.

23. A method for adjusting the location of a coated embryo within the uterus of a mammal comprising applying a magnetic field to said mammal containing said coated embryo, wherein said magnetic field is of sufficient strength to affect the location of said coated embryo.

24. The method of claim 23, wherein said coated embryo is located in proximity of the endometrium.

25. The method of claim 23, wherein said coated embryo is located at the uterine fundus of said mammal.

26. A method for preparing an embryo having improved stability in the uterus of a mammal comprising contacting said embryo with magnetic particles, wherein said magnetic particles attach to said embryo.

27. A method for stabilizing a mammalian egg within the uterus of a suitable mammal comprising:

(a) attaching magnetic particles to the external zona pellucida of said egg to generate a coated egg;

(b) transferring said coated egg into said uterus; and (c) applying a magnetic field to said mammal to stabilize said egg within said uterus.

28. The method of claim 27, wherein said egg is an unfertilized egg.

* * * * *